US008993793B1

(12) United States Patent
Lin et al.

(10) Patent No.: US 8,993,793 B1
(45) Date of Patent: Mar. 31, 2015

(54) MULTIFUNCTIONAL MESOPOROUS SILICA CATALYST

(75) Inventors: Victor Shang-Yi Lin, Ames, IA (US); Show-Ling Lee, legal representative, Ames, IA (US); Chih-Hsiang Tsai, Ames, IA (US); Hung-Ting Chen, Ames, IA (US); Marek Pruski, Ames, IA (US); Takeshi Kobayashi, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 405 days.

(21) Appl. No.: 13/361,613

(22) Filed: Jan. 30, 2012

Related U.S. Application Data (60) Provisional application No. 61/441,076, filed on Feb. 9, 2011.

(51) Int. Cl.
| | |
|---|---|
| C07C 51/43 | (2006.01) |
| C11C 3/00 | (2006.01) |
| B01J 31/16 | (2006.01) |
| C07C 67/08 | (2006.01) |

(52) U.S. Cl.
CPC . *C11C 3/003* (2013.01); *C11C 3/00* (2013.01); *B01J 31/1633* (2013.01); *C07C 67/08* (2013.01)
USPC ............ 554/174; 554/170; 554/168; 502/158

(58) Field of Classification Search
None
See application file for complete search history.

(56) References Cited

U.S. PATENT DOCUMENTS 7,122,688 B2 * 10/2006 Lin et al. ................. 554/169

OTHER PUBLICATIONS

Alvaro, M. et al., Nafion -functionalized mesoporous MCM-41 silica shows high activity and selectivity for carboxylic acid esterification and Rriedel-Crafts acylation reactions, 2005, Journal of Catalysis, vol. 231, pp. 48-55.*
Mbaraka, I.K., et al., Organosulfonic acid-functionalized mesoporous silicas for the esterification of fatty acid, 2003, Journal of Catalysis, vol. 219, pp. 329-336.*
Mbaraka, I.K., et al., Design of mltifunctionalized mesoporous silicas for esterification of fatty acid, 2005, Journal of Catalysis, vol. 229, pp. 365-373.*
Mbaraka, I.K., et al., Acidic Mesoporous Silica for the catalytic conversion of fatty acids in beef tallow, 2006, Ind. Eng. Chem. Res., vol. 45, pp. 3022-3028.*
Han, L. et al., Synthesis and characterization of the amphoteric amino acid bifunctional Mesoporous Silica, 2007, Chem Mater. vol. 19, pp. 2860-2867.*
Funatomi, T., et al., Pentafluorophenylammonium triflate (PFPAT): an efficient , practical, and cost-effective catalyst for esterificaitn, thioesterificatin, transesterification, and mcrolactone formation, 2006, Green Chemistry, vol. 8, pp. 1022-1027.*
Wakasugi, K., et al., Diphenylammonum triflate (DPAT): efficeint catalyst for esterificatin ofcarboxylic acids and for transesterification of carboxylic esters with nearly equimolar amounts of alcohol, 2000, Tetrahedron Letters, vol. 41, pp. 5249-5252.*

(Continued)

*Primary Examiner* — Yate K Cutliff
(74) *Attorney, Agent, or Firm* — Schwegman Lundberg & Woessner, P.A.

(57) ABSTRACT

The present invention provides bifunctional silica mesoporous materials, including mesoporous silica nanoparticles ("MSN"), having pores modified with diarylammonium triflate and perfluoroaryl moieties, that are useful for the acid-catalyzed esterification of organic acids with organic alcohols.

18 Claims, 4 Drawing Sheets

(56) References Cited

OTHER PUBLICATIONS

Abbasi, A., et al., "A novel highly acidic sulfonic functionalized SBA-1 cubic mesoporous catalyst and its application in the esterification of palmitic acid", Materials Science-Poland, 28(2), (2010), 565-572.

Li, Congming, et al., "Mesoporous oganosilicas containing disulfide moiety: Synthesis and generation of sulfonic acid functionality through chemical transformation in the pore all", Microporous and Mesoporous Materials 113, (2008), 333-342.

Liang, Xuezheng, et al., "Synthesis of a Novel Heterogeneous Strong Acid Catalyst from p-Toluenesulfonic Acid (PTSA) and its Catalytic Activities", Catal. Lett., 124, (2008), 352-356.

Mao, Kanmi, "Conformations of Silica-Bound (Pentafluorophenyl)propyl Groups Determined by Solid-State NMR Spectroscopy and Theoretical Calculations", J. Am. Chem. Soc. 132, (Aug. 13, 2010), 12452-12457.

Ngo, Helen L., et al., "Efficient Two-Step Synthesis of Biodiesel from Greases", Energy & Fuels, 22, (2008), 626-634.

Tsai, Chih-Hsiang, et al., "Multifunctional Mesoporous Silica Catalyst for Driving the Equilibrium Reaction to Completion by Removal of Byproduct", 241st ACS National Meeting and Exposition, Anaheim, CA, Mar. 27-31, 2011, Supporting Information, (2011), 8 pgs.

Tsai, Chih-Hsiang, et al., "Multifunctional Mesoporous Silica Catalyst for Driving the Equilibrium Reaction to Completion by Removal of Byproduct", 241st ACS National Meeting and Exposition, Anaheim, CA, Mar. 27-31, 2011, Abstract, (2011), 1 pg.

Tsai, Chih-Hsiang, et al., "Rational Catalyst Design: A Multifunctional Mesoporous Silica Catalyst for Shifting the Reaction Equilibrium by Removal of Byproduct", ACS Catal.,1(7), (2011), 729-732.

* cited by examiner

MULTIFUNCTIONAL MESOPOROUS SILICA CATALYST

REFERENCE TO RELATED APPLICATIONS

This application claims priority under 35 U.S.C. 119(e) from U.S. Provisional Application Ser. No. 61/441,076 filed Feb. 9, 2011, which is incorporated herein by reference in its entirety.

GOVERNMENT FUNDING

This invention was made with Government support of the United States Department of Energy under contracts DE-AC02-07CH11358 and DE-SC0001298. The United States Government has certain rights in this invention.

BACKGROUND OF THE INVENTION

Recently, advances have been made which strike a more desirable balance between maintaining fuel efficiency and reducing the percentage of particulate emissions in fuels through the use of blends of petroleum based fuel with alkyl esters of the fatty acids contained in vegetable oils or animal fats. These alkyl esters are commonly referenced to as "biodiesel". Substantially pure alkyl esters, such as methyl or ethyl esters of fatty acids, are generally preferred in biodiesel over the use of the vegetable oils and animal fats themselves because the alkyl esters have a viscosity that is more appropriate to diesel fuel. Through the use of these fuel blends, researchers have attained reductions in particulate emissions from diesel engines [1]. The production of biodiesel has received also extensive interest as a result of this fuel's desirable renewable, biodegradable, and nontoxic properties [2].

These fatty acid alkyl esters can be prepared by the transesterification of triglycerides in vegetable oils with short-chain alcohols (e.g., methanol and ethanol) using homogeneous alkali catalysts such as alkoxides. For example, soy diesel (methyl soyate) is made commercially by an energy and labor-intensive process wherein soybean oil is reacted with methanol at 140-150° F. (sometimes under pressure) in the presence of sodium methoxide. Isolation of the desired methyl soyate from the highly caustic (toxic) catalyst and other products such as glycerol, involves a precise neutralization process with strong acids, such as hydrochloric acid (HCl), and extensive washes with water to remove the resulting sodium chloride (NaCl) salt. Also, because of glycerol's high boiling point, it must be separated from the sodium chloride salt by vacuum distillation in an energy intensive operation. As more alkyl soyates with different alkyl functional groups, such as ethyl and isopropyl soyates, are being rapidly developed to meet the growing needs of various applications, the level of difficulty in separating the corresponding catalysts, e.g., sodium ethoxide and sodium isoproxide catalysts, respectively, will unavoidably escalate due to the increasing solubility of these basic catalysts in the reaction mixture. Therefore, biodiesel is currently not cost competitive with conventional diesel fuel.

To improve the economic outlook of biodiesel and alkyl esters in general, the feedstock selection becomes critical. In particular, feeds containing high free fatty acid content, such as found in beef tallow or yellow grease, are significantly less expensive than vegetable oils, such as soybean or rapeseed oil [3]. These high free fatty acid feedstocks present significant processing problems in standard biodiesel manufacture since the free fatty acid is saponified by the homogeneous alkali catalyst that is used to transesterify triglycerides leading to a loss of catalyst as well as increased purification costs [4].

One approach for improving the processing of high free fatty acid oils and fats is to first esterify the free fatty acids to alkyl esters in the presence of an acidic catalyst such as a mineral acid. The pretreated oils in which the free fatty acid content is lowered to no more than 0.5 wt % can then be processed under standard transesterification reaction conditions [5]. This pretreatment step has been successfully demonstrated using sulfuric acid [6]. Unfortunately, use of the homogeneous sulfuric acid catalyst adds neutralization and separation steps, as well as the esterification reaction, to the overall process.

Surfactant-templated mesostructured materials have received a great deal of attention as potential catalysts, sensors and adsorption agents owing to their combination of extremely high surface areas and ordered, flexible pore sizes. For example, mesoporous sieves of the type MCM-41 are prepared by thermal treatment of silaceous gels formed by the polymerization of alkoxysilanes around surfactant micelle templates in aqueous base, followed by removal of the surfactant to yield a matrix comprising fine pores in a cylindrical array. The physical and chemical properties of these mesoporous materials can be modified by incorporating functionalized organic groups, either by grafting on the preformed mesopore surface or by co-condensation using functionalized substituted trialkoxy silanes during synthesis [7-23]. Not only can such catalysts be easily separated from the products and recycled, but their large surface area (>700 m$^2$/g), defined pore structure, tunable pore diameter (2-10 nm) and narrow pore size distribution allow for precise regulation of the mass-transport properties that are crucial for many chemical transformations. Several recent studies have demonstrated that the selectivity and reactivity of MSN-supported catalysts can be enhanced by introducing multiple functional groups onto the 3D controlled mesoporous surface [8-11, 14, 16].

For example, organic-inorganic hybrid mesoporous silicas formed by co-condensation with thio-containing silanes, followed by oxidation of the SH groups yield pores functionalized with sulfonic acid groups. The direct co-condensation synthesis technique in which the mesostructure and functional group are simultaneously introduced, appears to be a desirable route for incorporating functional groups because it has been shown that it increases the concentration of the sulfonic groups in the mesoporous silica relative to post-formation grafting [24]. One approach demonstrated previously involves one-step synthesis based on the simultaneous hydrolysis and condensation of tetraethoxysilane (TEOS) with 3-(mercaptopropyl)trimethoxysilane (MPTMS) in the presence of template surfactant using in situ oxidation of the thiol groups with $H_2O_2$. Melero et al. has shown that the acid strength of the sulfonic groups in the mesoporous materials can be adjusted by choice of the organosulfonic precursor [25].

For example, mesoporous catalysts containing sulfonic acid groups and, optionally internal methyl groups have been reported to be efficient catalysts in the esterification of glycerol with fatty acids, where high yields of mono-esters are obtained [26].

Lin et al. (U.S. Pat. No. 7,122,688) discloses a method for transesterifying glyceride containing oils by combining a glyceride-containing vegetable or animal oil such as soy oil, a $C_1$-$C_3$ alcohol, and an acidic mesoporous silicate under conditions so that the mesoporous silicate catalyzes formation of the corresponding fatty acid ($C_1$-$C_3$) alkyl ester and optionally, glycerol, and wherein the silicate comprises sulfonic acids, sulfinic acids, phosphoric acids, phosphinic acids, boronic acids, selenic acids and mixtures thereof, linked to the silicate matrix by inert organic groups.

However, a continuing need exists for a simple method to form (lower)alkyl esters of fatty acids in the environment of triglyceride-containing feedstocks, particularly greases or fats that contain large amounts of free fatty acids mixed with triglycerides.

SUMMARY OF THE INVENTION

The present invention provides method for preparing esters from organic acids and alcohols and a catalyst for use in said preparation. The present method includes the preparation of fatty acid (C1-C3) alkyl esters in feedstocks comprising one or more fatty acid glycerol esters and one or more fatty acids (e.g. $C_7$-$C_{22}$ fatty acids), comprising combining the feedstock, a (C1-C3) alcohol, and the bifunctionalized acidic mesoporous silicate of the invention under conditions wherein the mesoporous silicate catalyzes the formation of the corresponding fatty acid (C1-C3) alkyl esters, and wherein the silicate comprises immobilized diarylammonium triflate groups and immobilized perfluoroaryl groups in the pores thereof. Preferably the diarylammonium triflate groups and the perfluoroaryl groups are linked to the pore surface via linkers such as inert organic groups, e.g., bivalent alkyl groups (—$(CH_2)_{2-6}$—), ($C_4$-$C_6$)alkenyl groups, fluoroalkyl groups and the like, wherein alkyl or alkenyl is optionally interrupted by —S—, —O—, —N(alkyl)-, arylene, and the like.

Therefore, the present invention also provides novel bifunctionalized mesoporous silica nanoparticles (MSN), containing diarylammonium triflate (DAT) groups and a pentafluorophenyl propyl (PFP) groups linked to the pores thereof.

It was discovered that, in esterification reactions, the reactivity of the bifunctional acidic MSN catalysts is proportional to the loading of immobilized PFP groups. This attributed to the extrusion of water molecules from the hydrophobic perfluorinated pores or "mesochannels" that drives the chemical equilibrium of a dehydration reaction to completion.

The benefits of using other secondary functional groups to increase the hydrophobicity of mesoporous catalysts have been already reported for several reactions involving dehydration.[30-32] The PFP functionality not only significantly enhances the catalytic activity in the esterification reaction, but performs better in this capacity than the commonly used trimethylsilyl group (TMS).

These bifunctionalized MSN catalysts also exhibited reactivity far superior than two industrially important solid acids, Amberlyst-15 and Nafion NR-50®, and were recyclable at least five times without losing activity.

BRIEF DESCRIPTION OF THE FIGURES

FIG. 2. TEM images of Cat A (a), Cat B (b), Cat C (c), and Cat D (d). Scale bars are 100 nm. The inset in (a) represents parallel mesoporous channels of Cat A. Scale bar=10 nm.

DETAILED DESCRIPTION OF THE INVENTION

Hereinbelow is described the synthesis and utilization of bifunctionalized silica mesoporous materials, such as mesoporous silica nanoparticles or "MSN," having pores modified with diarylammonium triflate and perfluoroaryl moieties. These catalysts can be employed for the acid-catalyzed esterification of organic acids ($R^1CO_2H$) with organic alcohols ($R^2OH$). $R^1$ and $R^2$ can be the same or different organic groups and can broadly include groups such as alkyl, alkenyl, aryl, aralkyl, alkaryl, alkaralkyl and the like, which can comprise substituents including 1-3 N, 5 or nonperoxide O, that do not react with, or otherwise bind to the diarylammonium sites or Si—OH sites of the silicate matrix, so as to interefere with the catalytic activity. Esterification of organic polyols and/or organic moieties containing a plurality of $CO_2H$ groups is also within the scope of the invention.

A preferred use of the present mesoporous materials are useful for the esterification of fatty acids with lower alkanols such as methanol or ethanol. For example, the esterification of fatty acids in high-free fatty acid oils and fats, can be used in the production of biodiesel.

Mesoporous Silicates

Particulate mesoporous silicates are preferred for use in the present method and typically have a particle size of about 50 nm to about 1 μm. In one embodiment, the mesoporous silicates have a particle size of at least about 100 nm, or preferably at least about 200 nm. In another embodiment, the mesoporous silicates have a particle size of less than about 750 nm, e.g., 300-500 nm diameter. As conventionally prepared, they are nearly spherical, e.g., elliptical in shape, with an aspect ratio of 1.5-2.0, but they have also been prepared under conditions that yield other shapes such as rods. The catalysts of the invention can include mesoporous silicate particles of any shape, provided the pore structure is suitable for accomodating the feedstock acids and/or esters.

The mesoporous silicate pores typically have a diameter of from about 1-100 nm. In one embodiment of the invention, the pores have a diameter of about 1-3 nm. In other embodiments, the pores have diameters of about ≥5 nm, or about ≥10 nm. Typically, the pores have a diameter of less than about 75 nm or less than about 50 nm. The surface area of the particles can be about 700-1000 $m^2/g$, e.g., 750-850 $m^2/g$.

The acidic mesoporous silicates can be prepared from aqueous dispersions of surfactant micelles of surfactants such as ($C_{10}$-$C_{20}$)alkylamines, ($C_{10}$-$C_{16}$)alkyl(tri(lower)alkyl)ammonium salts or Pluronic® surfactants in aqueous NaOH, followed by introduction of an alkyl orthosilicate, such as tetraethylorthosilicate (TEOS), and at least two functionalized silanes, comprising one or more diarylamine and one or more perfluoroaryl functional groups. The aryl groups are preferably phenyl groups, but can be ($C_6$-$C_{10}$)aryl groups, including indanyl, naphthyl, indenyl and the like. At least one of the aryl groups of the diaryl amino moiety, preferably the terminal aryl moiety, is hindered, such as by substitution with 1 to 5 lower ($C_1$-$C_3$)alkyl groups, methyl groups, and preferably comprises 2,4,6-trimethyl substitution. The perfluorylaryl functional group is preferably perfluorophenyl.

The aqueous mixture is stirred at moderate temperatures until the silicate precipitates, and it is collected and dried. The powder is then suspended in an organic solvent, e.g., toluene and treated with triflic acid, to introduce diarylammonium triflate sites. The particles are stirred under ambient conditions, filtered, washed with organic solvents and dried in vacuo. The surfactant "template" is then removed from the pores of the ordered silicate matrix, for example, by refluxing the silicate in aqueous-alcoholic HCl. The remaining solvent can be removed from the pores of the silicate by placing it under high vacuum and/or by heating. The functional groups incorporated on the surface of the pores can be quantified and optionally, can be removed or further modified as by oxidation, reaction with a protected acid equivalent followed by deprotection to yield the acidic silicate, and the like.

Figure 1:
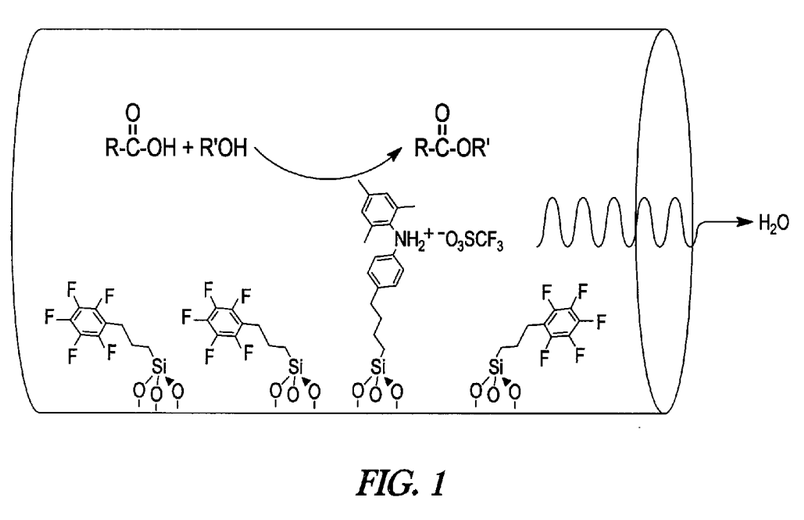
FIG. 1. Schematic representation of a bifunctional PFP/DAT MSN catalyst for esterification reaction.
Figure 2A:
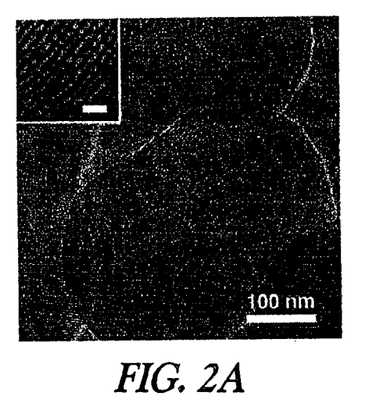
Figure 2B:
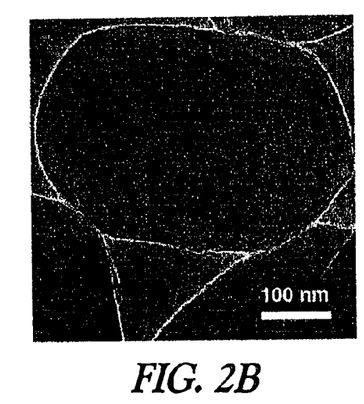
Figure 2C:
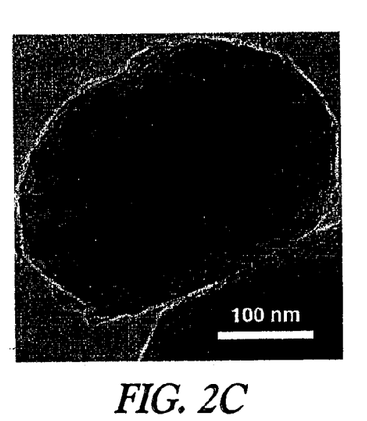
Figure 2D:
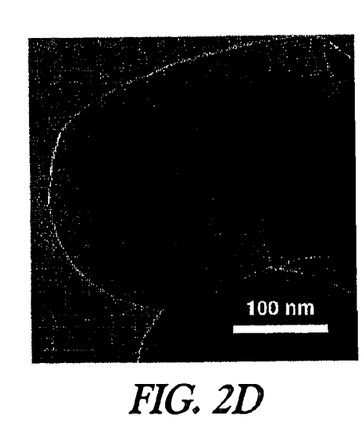

A representative bifunctionalized MSN catalyst containing a Brønsted acidic diaryl(alkyl)ammonium triflate (DAT) group and a 3-(pentafluorophenyl)propyl (PFP) functionality is schematically depicted in FIG. 1. The catalytic performance of these perfluorinated MSN-based solid acids was investigated and compared with other commercially available heterogeneous acid catalysts, such as Amberlyst-15 and Nafion NR-50®, in the esterification of different carboxylic acids, such as 4-phenylpropionic acid and heptanoic acid, with benzyl alcohol.

Rather than controlling the diffusional penetration of reactants to the catalytic sites inside the mesophores [11, 23], the PFP groups (perfluorophenyl groups) were incorporated into the porous framework, so that the perfluorinated, water-resistant mesochannels could efficiently extrude water molecules produced during the esterification reaction (FIG. 1).

A detailed study of the conformations of silica-bound PFP groups by solid-state NMR spectroscopy and theoretical calculations have been described separately [27].

It is believed that this is the first demonstration of enhancing chemical transformation by expelling byproducts from the mesoporous catalytic center and further driving the reaction equilibrium forward according to the Le Chatelier's principle.

A diarylamine-functionalized alkoxysilane (DAS), N-(4-(4-(diethoxymethylsilyl)butyl)phenyl)-2,4,6-trimethylaniline (2), was first synthesized as a precursor for the synthesis of the aforementioned bifunctionalized MSN materials as shown in Scheme 1.

The 4-(4-bromophenyl)-1-butene was coupled with trimethylaniline through a palladium-mediated amination to yield a diarylamine 1, followed by a hydrosilylation reaction with methyldiethoxysilane to synthesize the desired DAS compound 2.

Two bifunctionalized MSN catalysts were prepared by introducing DAS and 3-(pentafluorophenyl)propyl-trimethoxysilane (PFP-TMS) in molar ratios 1:1 (Cat A) and 1:4 (Cat B), to a NaOH-catalyzed, CTAB-templated co-condensation reaction of tetraethoxysilane, as detailed in the Examples. Additionally, two monofunctionalized MSN catalysts with only the DAS (Cat C) and the PFP (Cat D) group were synthesized via the same method. After the removal of CTAB, these MSN catalysts were treated with triflic acid to yield the desired Brønsted acidic DAT group. The physisorbed triflic acid on the surface was removed under vacuum, as indicated by the TGA analysis and $^{19}$F solid-state NMR spectra of the resulting materials.

The TEM images showed that all particles exhibited an elliptical shape with the aspect ratio of 1.5-2.0 and average length of 350-400 nm, as shown in FIG. 2. The mesoporous channels were arranged in 2D hexagonal array, as observed by TEM and powder X-ray diffraction (XRD). These studies indicated that the porous structure of these MSN materials remained intact after the treatment with triflic acid. The $N_2$ sorption analysis of the samples showed a type IV isotherm, which is characteristic of a cylindrical mesoporous structure. The measured BET surface areas of Cat A, B, C, and D were 792.1, 861.3, 816.2 and 837.4 m$^2$/g, respectively. The average pore size calculated using the BJH method is 2.5±0.2 nm for all material, as summarized in Table 1.

TABLE 1

Textural properties of MSN catalysts

| Sample | Surface area (m$^2$/g)$^a$ | Average pore diameter (nm)$^b$ |
|---|---|---|
| Cat A | 792.1 | 2.6 |
| Cat B | 861.3 | 2.4 |
| Cat C | 816.2 | 2.7 |
| Cat D | 837.4 | 2.4 |

$^a$The specific surface area is calculated using the BET method.
$^b$The average pore diameter is measured by the BJH method.

The total concentration of covalently bound surface organic functionalities was evaluated by solid-state $^{29}$Si NMR, based on the relative intensities of resonances representing Q$''$, T$''$, and D$''$ sites, as summarized in Table 2.

TABLE 2

Loading and relative ratio of organic functional groups in the MSN catalysts based on quantitative solid-state $^{29}$Si MAS NMR.

| Sample | PFP (mmol/g) | DAT (mmol/g) | PFP:DAT ratio |
|---|---|---|---|
| Cat A | 0.70 (35%)[a] | 0.12 | 6:1 |
| Cat B | 0.76 (35%)[a] | 0.05 | 15:1 |
| Cat C | 0 | 0.30 | NA |
| Cat D | 0.62 (30%)[a] | 0 | NA |

[a]Surface coverage of PFP, calculated assuming that the inner pore surface area in MSNs constitutes 90% of the total surface, and the footprint area of the PFP compound is ~0.6 nm². The DAT groups were not included.

Figure 3:
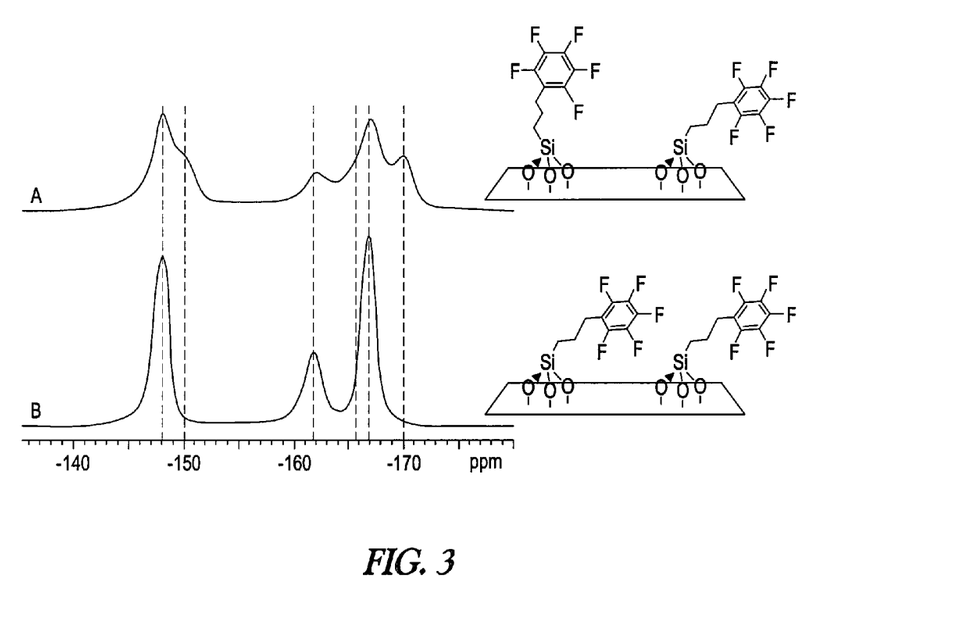
FIG. 3. $^{19}F$ solid-state MAS NMR spectra of PFP-MSN (Cat D) measured in dried condition (a) and with mesopores filled with heptane (b). The dotted lines indicate resonances representing fluorines in 'prone' and 'upright' PFP functionalities, which are depicted on the right side of the figure. In the presence of solvent, all molecules remain "prone," or close to the silica surface.

The $^{13}$C CPMAS NMR spectra were measured to confirm the covalent immobilization of all functional groups and the integrity of their chemical structures. In a sample equivalent to Cat D, which was studied in the 'dry' state (i.e. in the absence of solvent inside the pores), the silica-bound PFP groups assume two different conformations: the molecules located in the proper vicinity of accessible siloxane groups take on prone orientation, with the aromatic rings centered near the siloxane oxygens, whereas the remaining PFP functionalities are oriented roughly upright with respect to the silica surface [27]. Both structures were determined by a number of 2D solid-state NMR experiments and further substantiated by theoretical calculations. In particular, the fingerprints of both conformations were obtained in terms of $^{19}$F chemical shifts (FIG. 3a). Upon further examination of this system, we found that the conformations of PFP groups can change when the pores are filled with a solvent. Indeed, in the presence of heptane, only the resonances representing molecules in prone positions are detected (FIG. 3b). Thus, the introduction of the secondary PFP groups can have a beneficial effect on the esterification reaction by creating a non-wettable hydrophobic environment on the inner surface of the MSNs.

Figure 4:
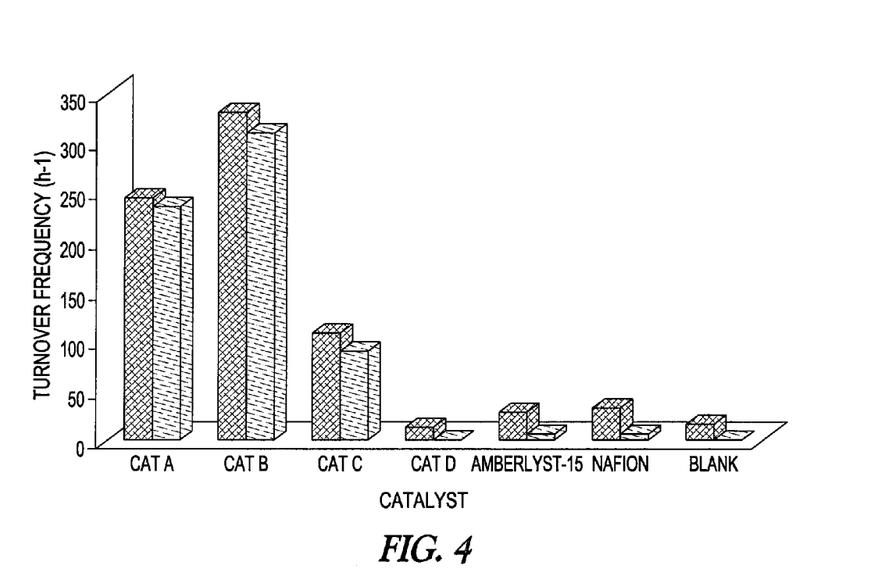
FIG. 4. Esterification reactions of 3-phenylpropionic acid (left bar) and heptanoic acid (right bar) with benzyl alcohol catalyzed by various heterogeneous acid catalysts (0.2 mol % catalysts, 0.4 M sustrate conc. in heptanes).

To investigate the effect of PFP groups on the catalytic performance of DAT, catalysts A-D were tested in the esterification reactions of 3-phenylpropionic acid or heptanoic acid with benzyl alcohol in heptane. As illustrated in FIG. 4, the bifunctionalized PFP/DAT MSNs (Cat A and Cat B) exhibit the best reactivity of all catalysts. The turnover frequency (TOF) of Cat B is higher than that of Cat A, which may be attributed to the higher relative concentration of PFP. The TOF of Cat C is considerably lower than those of Cat A and Cat B, which shows that the DAT groups alone are less efficient in both esterifications. Cat D exhibits negligible activity, i.e. the PFP groups do not catalyze these reactions.

To compare the effect of PFP with other commonly used hydrophobic groups, the surface of Cat C was further passivated with a TMS group to make the TMS/DAT MSN material. The esterification reaction yield of methyl 3-phenylpropionate catalyzed by TMS/DAT MSN (57%, corresponding to TOF=190 h$^{-1}$) was slightly higher than that of Cat C, but proved to be lower than observed in Cat A and Cat B. We also note that the reaction of 3-phenylpropionic acid and benzyl alcohol catalyzed by homogeneous triflic acid under the same conditions only gave 18.3% of yield (TOF=61.3 h$^{-1}$). Given the low reactivity and high acidity (pKa=−14) of triflic acid, this result indicates that the acid strength of the catalyst is not the only factor affecting the equilibrium of this reaction.[34]

The enhancement of catalytic properties observed in bifunctional catalysts Cat A and Cat B is attributed to the aforementioned formation of a surface-bound layer of PFP molecules, whose prone orientation in the presence of heptanes prevents direct interaction between water and the surface silanol groups. In spite of the incomplete PFP coverage (see Table 2), the catalyst surface becomes sufficiently hydrophobic to effectively force the water molecules out of the mesopores and thereby drive the chemical equilibrium toward the completion of the esterification reaction. Indeed, following the reaction the amount of water byproduct observed on the walls of reaction tubes containing Cat A and Cat B was much higher than for Cat C and TMS/DAT-MSN. Cat D did not produce any water due to its negligible activity.

Figure 5:
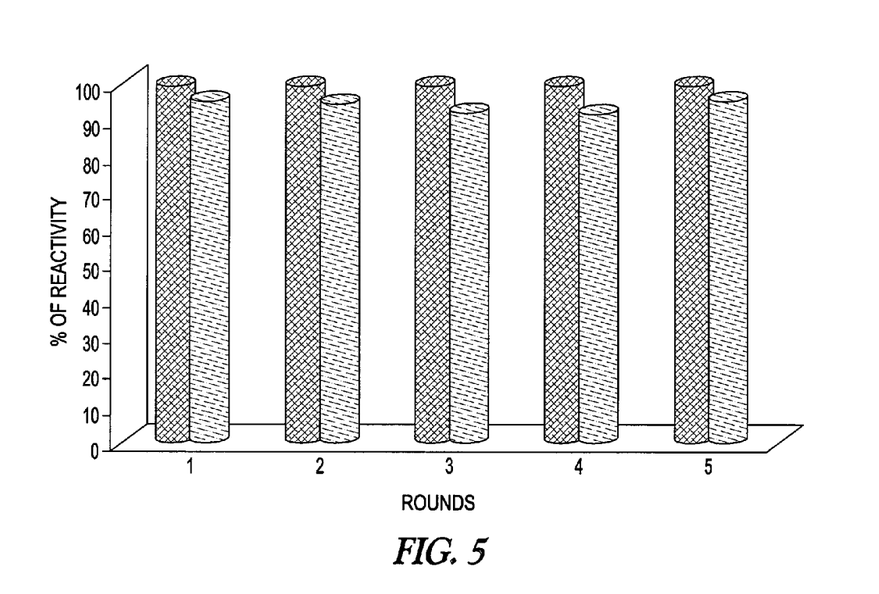
FIG. 5. Recyclability of Cat B in five successive runs of esterification of 3-phenylpropionic acid with benzyl alcohol. The left and right bars represent the reaction conversion and yield, respectively. Reaction condition: [Acid]=[alcohol]= 0.38 M in heptane, 0.4 mol % Cat B, 70° C. for 2 h.

The bifunctional PFP/DAT MSNs and DAT-MSN proved to be recyclable at least five times with identical leads as shown in FIG. 5, indicating that the reactivity difference between bi- and mono-functional catalysts is not due to the decomposition of DAT groups. The pKa values of all relevant chemical species in this catalytic system do not favor the proton transfer from these groups.[33] Finally, all studied DAT-MSNs showed higher reactivity than the commercial polymeric solid acid catalysts Amberlyst-15 and Nafion NR-50® under the examined reaction conditions. It is noted, however, that Amberlyst-15 and Nafion NR-50® use a different functionality (sulfonic acid), for which the conditions used in these tests were not optimized. Although these resin-based catalysts bear high density of acid sites,[28] they often require the use of swelling solvents to enhance the accessibility of reactants to these sites.[29]

The present bifunctional MSN catalytic system exhibits superior reactivity in the equilibrium reaction. The remarkable yields are the result of a nanoenvironment designed to expel the byproduct (water) by the secondary functional group.

The invention will be further described by reference to the following detailed examples, wherein all chemicals were used as received without further purification. Organosilanes, which included tetraethylorthosilicate (TEOS), methyldiethoxysilane, and 3-(pentafluorophenyl)propyl trimethoxysilane (PFP-TMS) were purchased from Gelest, Inc. Other chemical reagents were purchased from Sigma-Aldrich, Inc.

Example 1

Synthesis of Diarylamine Organosilane (DAS)

1

-continued

1.1 Synthesis of 4-(4-Bromophenyl)-1-butene

A 250 ml two-necked round-bottom flask, equipped with an additional funnel and condenser, was charged with 4-bromo-benzyl bromide (20.0 g, 80 mmol) in 50 ml dry ether at 0° C. ice bath for 10 min. The allylmagnesium chloride (48.0 ml of a 2.0 M solution in ether, 96 mmol) was added dropwisely via an additional funnel over a period of 30 min at 0° C. Subsequently, the mixture was stirred at room temperature for 2 h and refluxed for another 3 h. The reaction was monitored by TLC analysis. After the starting material disappeared, the reaction was quenched by water and transferred to a separation funnel. The organic layer was washed with brine, dried over anhydrous $MgSO_4$, and then concentrated under vacuum to yield a yellow crude liquid. The product was purified by Kugelrhor distillation to obtain the final product as a transparent liquid (14.10 g, 83%), whose $^1H$ and $^{13}C$ NMR spectra matched with the earlier reported literature data [7].

1.2 Synthesis of N-(4-(but-3-en-1-yl)phenyl)-2,4,6-trimethylaniline (1)

A mixture of $Pd_2(dba)_3$ (517.6 mg, 5 mol % Pd), BINAP (1.06 g, 1.5 eq of Pd), and potassium tert-butoxide (3.05 g, 27.13 mmol) in 80 ml toluene was prepared in a round-bottom flask in a glove box. The 4-(4-bromophenyl)-1-butene (5.00 g, 22.6 mmol) and 2,4,6-trimethylaniline (3.80 ml, 27.13 mmol) were added by syringe, and the reaction mixture was stirred at 80° C. oil bath for 12 h. The mixture was quenched with a saturated $NaHCO_{3(aq)}$ solution and then concentrated under reduced pressure. The crude product was purified by column chromatography (t-butyl methyl ether/heptane (v/v)=3/97, Rf=0.3) to afford N-(4-(but-3-en-1-yl)phenyl)-2,4,6-trimethylaniline (4.83 g, 76.7%). $^1H$ NMR (300 MHz, $CDCl_3$): δ 6.95 (m, 4H), 6.44 (s, 1H), 6.42 (s, 1H), 5.87 (m, 1H), 5.01 (m, 2H+NH), 2.60 (t, 2H), 2.30 (s, $^1H$), 2.17 (s, 6H). $^{13}C$ NMR (100 MHz, $CDCl_3$): δ 144.7, 138.8, 135.6, 135.2 (2C), 134.8, 131.5, 129.4 (2C), 129.2 (2C), 114.8, 113.6 (2C), 36.1, 34.8, 21.1, 18.5 (2C). MS (EI): m/z: calc. for $C_{19}H_{23}N$: 265.18. found 265.18.

1.3 Synthesis of N-(4-(4-(diethoxy(methyl)silyl)butyl)phenyl)-2,4,6-trimethylaniline (2)

Compound 1 (5 g, 18.8 mmol) and 15 ml of methyldiethoxysilane were placed in a Schlenk tube under argon. The platinum oxide, $PtO_2$ (20 mg, 478 ppm), was added to the mixture, and the tube was sealed and heated at 85° C. for 20 h. After cooling to room temperature, the crude product was diluted with anhydrous ethanol and filtered through activated charcoal to remove $PtO_2$. The filtrate was concentrated at reduced pressure and purified by column chromatography (ethyl acetate/heptane=2.5/97.5, Rf=0.38) to afford the compound 3 (4.82 g, 65.7% yield). $^1H$ NMR (300 MHz, $CDCl_3$): δ 7.28 (dd, 2H), 7.26 (s, 2H), 6.94 (dd, 2H), 5.02 (s, NH), 3.74 (t, 4H), 2.49 (t, 3H), 2.30 (s, 3H), 2.16 (s, 6H), 157 (m, 2H), 1.41 (m, 2H), 121 (t, 6H), 0.64 (t, 2H), 0.10 (s, 3H). $^{13}C$ NMR (100 MHz, $CDCl_3$): δ 144.6, 136.2, 135.8 (2C), 135.2, 132.4, 129.4 (4C), 113.6 (2C), 58.3 (2C), 35.5, 34.9, 22.8 (2C), 21.1, 18.6 (2C), 13.9 (2C), −4.6. MS (EI): m/z calc. for $C_{24}H_{37}NO_2Si$: 399.26. found 399.26.

Example 2

Synthesis of Bifunctionalized PFP/DAT.MSN Catalysts

The functionalized MSNs were synthesized via a reported co-condensation method [11]. Typically, a mixture of cetyl trimethyl ammonium bromide (CTAB) (1.0 g. 2.75 mmol) and 2.0 M of $NaOH_{(aq)}$ (3.5 ml, 7.0 mmol) in 240 ml $H_2O$ was heated at 80° C. for 30 min. To this clear solution tetraethoxysilane (5 ml, 22.4 mmol). PFP-TMS (0.44 g, 1.44 mmol), and/or DAS organosilane (2) (0.58 g, 1.44 mmol) were injected rapidly and sequentially to yield an opaque reaction mixture. The resulting reaction mixtures were stirred at 80° C. for 2 h. The as-made MSNs were obtained after hot filtration, followed by washing with copious amount of water and methanol, and drying under vacuum. The surfactant was removed by stirring the solution of as-made materials (1.0 g) and 0.8 ml of concentrated HCl in 100 ml methanol at 60° C. for 6 h. The resulting surfactant-free MSNs were filtered, washed with water and methanol, and dried under vacuum for 24 h.

The trifluoromethanesulfonic acid (TFA) ("triflic acid") (0.27 ml, 3 mmol) was added to a suspension of the MSN materials (0.2 g) in dry toluene (10 ml, 94.1 mmol), and stirred at room temperature for 6 h. The solid powder was filtered and washed with copious amount of toluene, hexane, ether, and dried under vacuum for 12 h at room temperature. Finally, the resulting powder was heated at 135° C. under the vacuum (<1 mm Hg) for 18 h to remove the excess amount of physisorbed acid remaining on the silica surface. The resulting MSN catalysts were then sealed in scintillation vials and stored in a desiccator.

Example 3

Synthesis of TMS/DAT-MSN Catalyst

Typically, a 50 ml round-bottom flask charged with the surfactant-free DAS-MSNs (0.3 g) was pre-dried under vacuum at 90° C. for 6 h to remove the physisorbed moisture. A solution of HMDS (1.25 ml, 6 mmol) in dry toluene (15 ml) was injected into the reaction flask. The reaction was then stirred to 60° C. for 24 h. The solid product was isolated by filtration, followed by washing with 200 ml of toluene and 50 ml of methanol, and dried under high vacuum for 24 h. The acid treatment with TFA of this TMS/DAS-MSN sample was following the same method described hereinabove. The TMS/DAT MSN exhibited 685 $m^2/g$ of specific surface area estimated from BET method and 2.2 nm of mean pore diameter. The loading of DAT group in this material, calculated via $^1H$ DPMAS NMR, was 0.16 mmol/g. The loading of TMS was calculated to be 2.2 mmol/g.

Example 4

Catalytic Esterification Reactions

The reactions were carried out using an equal amount of catalytic sites in a capped tubular reactor. For example, the reaction mixture consisting of heptanoic acid (49.8 mg, 0.383 mmol), benzyl alcohol (41.4 mg, 0.383 mmol) and catalysts (0.2 mol %) in 1 ml of heptanes was heated at 60° C. for 1.5 h. The catalysts were isolated by centrifuge and washed with 10 ml of heptane.

Diphenyl ether (ca. 100 mg), was added into the combined heptane solution as an internal standard. The reaction conversion and product yield were determined by gas chromatography using a HP-5 column. The oven temperature was initially set at 40° C. for 4 min, then increased to 250° C. with a ramp rate of 10° C./min, and kept at 250° C. for 5 min.

The peaks corresponding to all reagents and products were separated, and their integrated intensities were calibrated using an internal standard. For the recyclability test, the reaction mixture of 3-phenylpropanoic acid (57.5 mg. 0.383 mmol), benzyl alcohol (41.4 mg, 0.383 mmol), and 0.4 mol % of Cat B in 1 ml of heptane was stirred at 70° C. for 2.5 h. The filtered catalyst was dried under vacuum for 24 h and recharged with the same amount of starting material for each run.

REFERENCES

The documents listed below are incorporated by reference herein as though fully set forth.

[1] M. Bender, *Bioresource Technol.*, 70, 80 (1999); M Diasakou et al., *Fuel*, 77, 1297 (1998); T. Ogoshi et al., *J. Am. Oil Chem. Soc.*, 62, 331 (1985)
[2] G. J. Suppes et al., *J. Am. Oil Chem. Soc.*, 78, 839 (2001); G. Kildrian et al., op. cit., 73, 225 (1996); J. Encinar et al., *Ind. Eng. Chem. Res.*, 38, 2927 (1999).
[3] F. Ma et al., *Ind. Eng. Chem.*, 37, 3768 (1998).
[4] D. G. B. Boocock et al., *J. Am. Oil Chem. Soc.*, 75, 1167 (1998).
[5] H. N. Basu et al. (U.S. Pat. No. 5,525,126).
[6] S. Koona et al, European Patent No. 566087 (1993).
[7] M. Alvaro et al., *Chem. Commun.*, 956 (2004)
[8] S. Angloher et al., *Microporous Mesoporous Mater.*, 115, 629 (2008).
[9] A. Corma et al., *Chem. Rev.*, 103, 4307 (2003).
[10] A. Kuschel et al., *J. Am. Chem. Soc.*, 132, 6558 (2010).
[11] S. Huh et al., *J. Am. Chem. Soc.*, 126, 1010 (2004); V. S.-Y. Lin et al. (U.S. Pat. No. 7,122,688).
[12] E. L. Margelefsky et al., *J. Am. Chem. Soc.*, 129, 13691 (2007).
[13] A. Schlossbauer et al., *J. Am. Chem. Soc.*, 130, 12558 (2008).
[14] K. K. Sharma et al., *Angew. Chem.*, 119, 2937 (2007); *Angew. Chem. Int. Ed.*, 46, 2879 (2007).
[15] H. L. Ngo et al., *Energy Fuels*, 22, 626 (2008).
[16] S. Huh et al., *Angew. Chem.*, 117, 1860 (2005); *Angew. Chem. Int. Ed.*, 44, 1826 (2005).
[17] M. W. McKittrick et al., *J. Am. Chem. Soc.*, 126, 3052 (2004).
[18] S. Shylesh et al., *Angew. Chem.*, 122, 188 (2010); *Angew. Chem. Int. Ed.*, 49, 184 (2010).
[19] E. L. Margelefsky et al., *Chem. Soc. Rev.*, 37, 1118 (2008).
[20] S. Shylesh et al., *Chem.-Eur. J.*, 15, 7052 (2009).
[21] D. J. Mihalcik et al., *Angew. Chem.*, 120, 6325 (2008); *Angew. Chem. Int. Ed.*, 47, 6229 (2008).
[22] Y. Huang et al., *New J. Chem.*, 32, 1311 (2008).
[23] A. Anan et al., *J. Mol. Catal. A. Chem.*, 288, 1 (2008).
[24] I. Diaz et al., *Stud. Sanf. Sci. Catal.*, 135, 1288 (2001).
[25] J. A. Melero et al., *J. Mater. Sci.*, 12, 1664 (2006).
[26] W. D. Bossaert et al., *J. Catal.*, 182, 156 (1999); I. Diaz et al., *Appl. Catal.*, 242, 161 (2003); I. Diaz et al., *J. Catal.*, 193, 295 (2000); D. Magolese et al., *Chem. Mater.*, 12, 2448 (2000).
[27] K. Mao et al., *J. Am. Chem. Soc.*, 132, 12452 (2010).
[28] R. Kunin et al., *Ind. Eng. Chem. Prod. Res. Dev.*, 1, 140 (1962).
[29] P. F. Siril et al., *J. Mol. Catal. A: Chem.*, 279, 63 (2008); G. Gebel et al., *Polymer*, 34, 333 (1993).
[30] I. Diaz et al., *J. Catal.*, 193, 295 (2000).
[31] I. K. Mhara et al., *J. Catal.*, 229, 365 (2005).
[32] J. P. Daquin et al., *Green Chem.*, 12, 1383 (2010).
[33] The pKa values of triflic acid, protonated carboxylic acid, protonated alcohol and DAT salt are −14, −6 to −7, −2 and 1, respectively. (M. B. Smith, J. March, *March's Advanced Organic Chemistry*, Sixth ed., Wiley-interscience, 2007). The surface diphenylamine (DAS) group treated with triflic acid resulted in proton transfer to form the diphenylammonium (DAT) salt quantitatively. Thus, only limited amount of protons could have been transferred from DAT groups to acids and alcohols in the catalysts studied in this work.
[34] K. Ishihara et al., *J. Am. Chem. Soc.*, 127, 4168 (2005).

All publications, patents and patent applications cited hereinabove are incorporated herein by reference. While in the foregoing specification this invention has been described in relation to certain preferred embodiments thereof, and many details have been set forth for purposes of illustration it will be apparent to those skilled in the art that the invention is susceptible to additional embodiments and that certain of the details described herein may be varied considerably without departing from the basic principles of the invention.

What is claimed is:

1. A method for preparing an ester, comprising combining an organic acid, an alcohol, and an acidic mesoporous silicate under conditions wherein the mesoporous silicate catalyzes the formation of the ester of the acid and the alcohol and wherein the silicate comprises diarylammonium triflate groups and perfluoroaryl groups in the pores of said silicate, wherein said groups are linked to the silicate matrix by inert organic groups.

2. A method for preparing a fatty acid ($C_1$-$C_3$) alkyl ester from a fatty acid comprising combining a fatty acid, a ($C_1$-$C_3$) alcohol, and an acidic mesoporous silicate under conditions wherein the mesoporous silicate catalyzes formation of the corresponding ($C_1$-$C_3$) alkyl ester, and wherein the silicate comprises diarylammonium triflate groups and perfluoroaryl groups in the pores thereof, wherein said groups are linked to the silicate matrix by inert organic groups.

3. A method for preparing fatty acid ($C_1$-$C_3$) alkyl esters from a feedstock comprising one or more fatty acid glycerol esters and one or more fatty acids comprising combining the feedstock, a ($C_1$-$C_3$) alcohol, and an acidic mesoporous silicate under conditions wherein the mesoporous silicate catalyzes the formation of the corresponding fatty acid ($C_1$-$C_3$) alkyl esters, and wherein the silicate comprises diarylammonium triflate groups and perfluoroaryl groups in the pores thereof, wherein said groups are linked to the silicate matrix by inert organic groups.

4. The method of claim 1, 2 or 3 wherein the said diarylammonium triflate groups comprise 2,4,6-trimethylphenyl (phenyl) ammonium triflate moieties.

5. The method of claim 1, 2 or 3 wherein the perfluoroaryl groups are pentafluorophenyl groups.

6. The method of claim 1, 2 or 3 wherein the acidic mesoporous silicate is in the form of particles having a diameter of about 100-500 nm.

7. The method of claim 1, 2 or 3 wherein the pores have a diameter of about 1-5 nm.

8. The method of claims 2 or 3 wherein the fatty acid comprises a $C_7$-$C_{22}$ fatty acid.

9. The method of claim 3 wherein the ester is a tri-ester of glycerol.

10. The method of claim 9, wherein the tri-ester comprises one or more $C_8$-$C_{22}$ fatty acid esters.

11. The method of claim 2 wherein the fatty acid glycerol ester is a glyceride in an animal fat or oil.

12. The method of claim 11 wherein the fatty acid glycerol ester is a glyceride in a vegetable oil.

13. The method of claim 1, 2 or 3 wherein the alcohol is methanol or ethanol.

14. The method of claim 13 wherein the alcohol is methanol.

15. The method of claim 1, 2 or 3 wherein the formation of the ester is carried out at a temperature of less than about 150° C.

16. The method of claim 1, 2 or 3 wherein the inert organic groups are ($C_2$-$C_{10}$)alkyl.

17. The method of claim 1, 2 or 3 wherein aryl is ($C_6$-$C_{10}$) aryl.

18. The method of claim 1, 2 or 3 wherein aryl is phenyl.

* * * * *